United States Patent [19]

Mann et al.

[11] Patent Number: 5,514,164
[45] Date of Patent: May 7, 1996

[54] DDD PACING RESPONSE TO ATRIAL TACHYUCARDIA AND RETROGRADE CONDUCTION

[75] Inventors: Brian M. Mann, Beverly Hills; John W. Poore, South Pasadena, both of Calif.

[73] Assignee: Pacesetter, Inc., Sylmar, Calif.

[21] Appl. No.: 217,577

[22] Filed: Mar. 25, 1994

[51] Int. Cl.$^6$ .................................................. A61N 1/368
[52] U.S. Cl. ................................................ 607/25; 607/14
[58] Field of Search .................................... 607/9, 14, 25

[56] References Cited

U.S. PATENT DOCUMENTS

| | | | |
|---|---|---|---|
| 4,429,697 | 2/1984 | Nappholz et al. | 128/419 |
| 4,554,920 | 11/1985 | Baker et al. | 128/419 |
| 4,572,193 | 2/1986 | Mann et al. | 128/419 |
| 4,712,555 | 12/1987 | Thornander, et al. | 128/419 |
| 4,712,556 | 12/1987 | Baker | 128/419 |
| 4,788,980 | 12/1988 | Mann et al. | 128/419 |
| 4,809,697 | 3/1989 | Causey et al. | 128/419 |
| 4,856,523 | 8/1989 | Sholder et al. | 128/419 |
| 4,880,005 | 11/1989 | Pless et al. | 128/419 |
| 4,940,052 | 7/1990 | Mann et al. | 128/419 |
| 4,944,298 | 7/1990 | Sholder | 128/419 |
| 4,944,299 | 7/1990 | Silvian | 128/419 |
| 5,074,308 | 12/1991 | Sholder et al. | 128/697 |
| 5,144,949 | 9/1992 | Olson | 128/419 |
| 5,228,438 | 7/1993 | Buchanan | 128/419 |
| 5,273,035 | 12/1993 | Markowitz et al. | 607/14 |
| 5,395,397 | 3/1995 | Lindgren et al. | 607/14 |

*Primary Examiner*—William E. Kamm
*Assistant Examiner*—Kennedy J. Schaetzle
*Attorney, Agent, or Firm*—Malcolm J. Romano; Harold C. Schloss

[57] ABSTRACT

An implantable pacemaker operates in a DDD mode and reverts to a modified DDI mode in response to sensing atrial depolarization early in the pacing cycle. The modified DDI mode, when invoked, provides additional atrial kick by generating an atrial stimulation pulse (A-pulse) when there is sufficient time left in the current pacing cycle for the atrial kick resulting from such A-pulse to be of hemodynamic and electrophysiologic benefit. A time window, $T_A$, is defined that follows the post-ventricular atrial refractory period (PVARP) of the normal DDD pacing cycle. If a P-wave is sensed during $T_A$, then the modified DDI mode is invoked. In such modified DDI mode, the time between the last ventricular event and the next scheduled V-pulse, absent the detection of an inhibiting R-wave, is preserved. Further, in such modified DDI mode, if there is sufficient time to supply an A-pulse before the next V-pulse is scheduled, such A-pulse will be generated to provide the additional atrial kick. In one embodiment, if there is more than a fixed time interval e.g., 300 msec, plus a programmed AV delay (AVD) time remaining before the next scheduled V-pulse after sensing a P-wave during the time window $T_A$, then an A-pulse is generated one AVD time prior to the next scheduled V-pulse.

47 Claims, 5 Drawing Sheets

FIG. 1
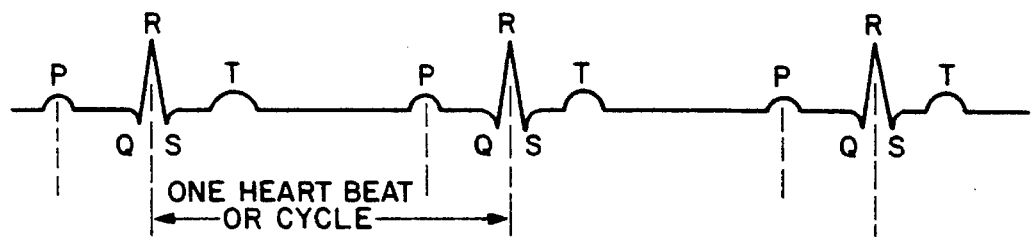
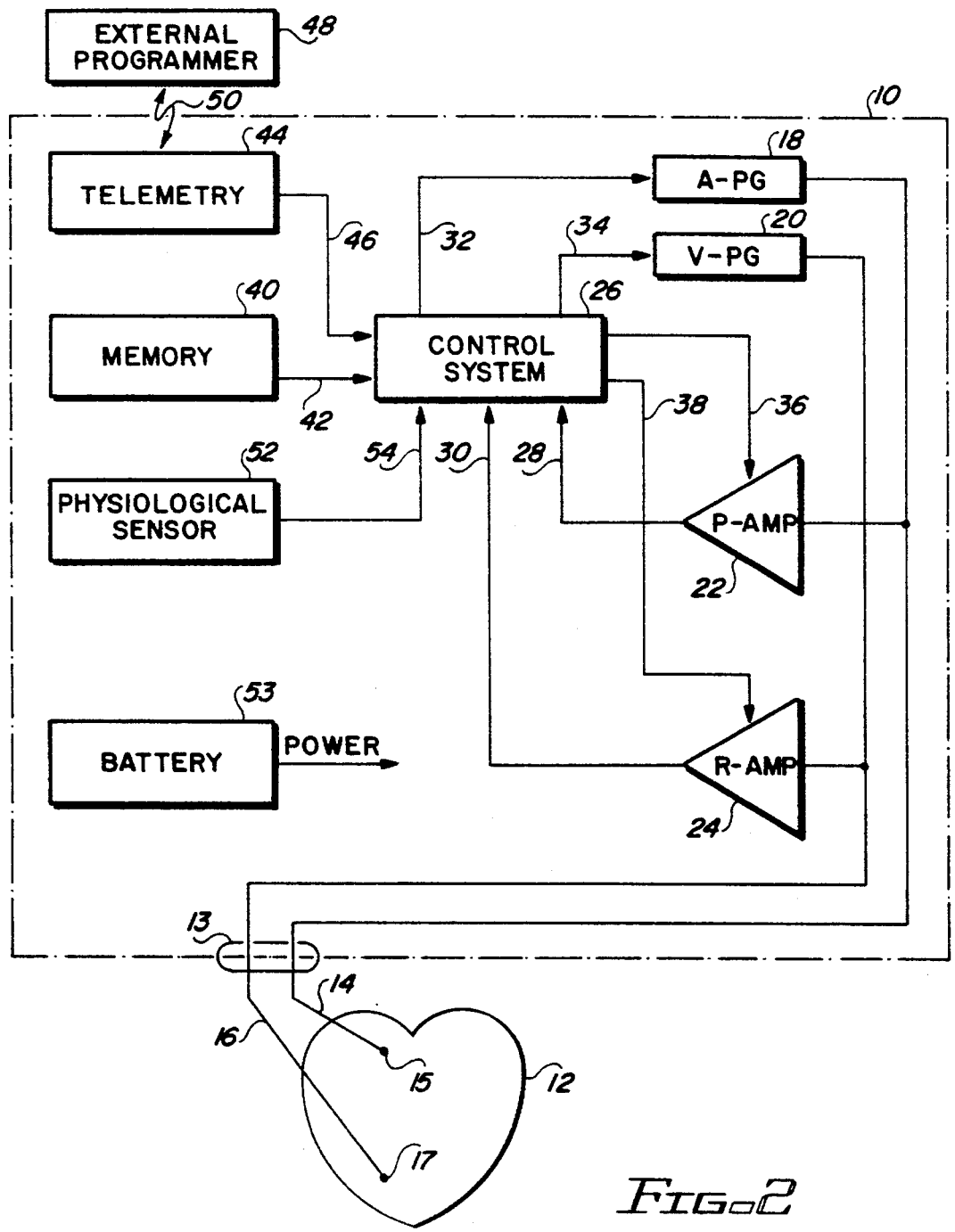
FIG. 2

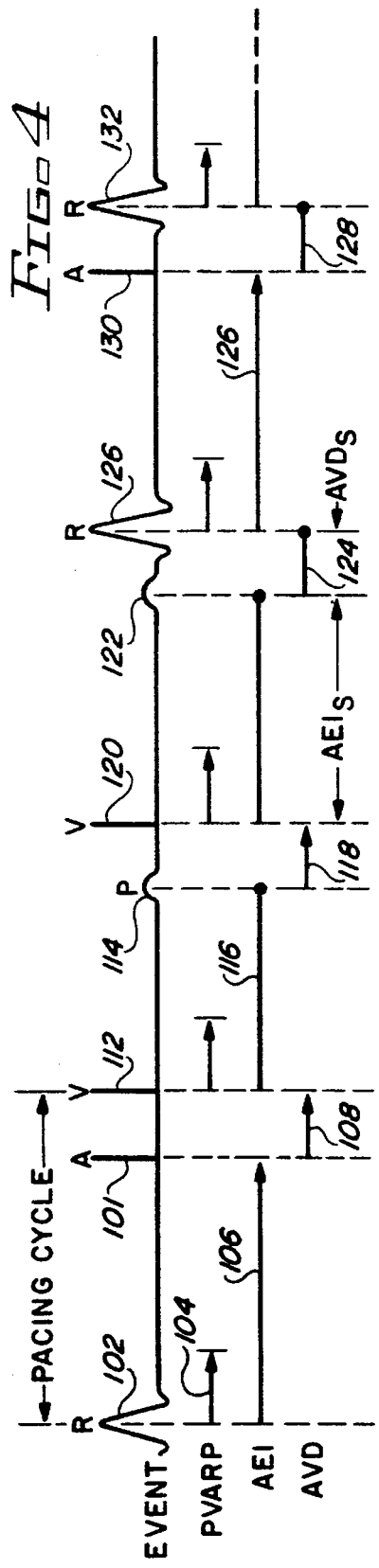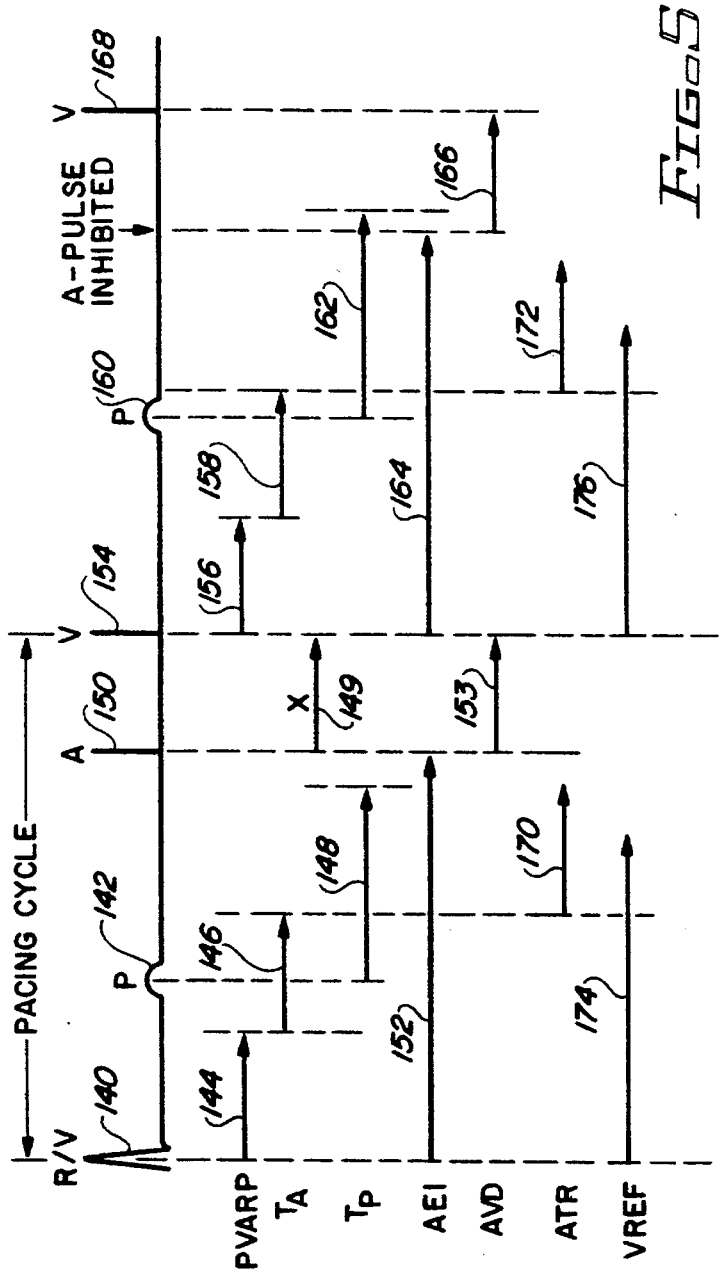

DDD PACING RESPONSE TO ATRIAL TACHYUCARDIA AND RETROGRADE CONDUCTION

BACKGROUND OF THE INVENTION

1. Field of the Invention

The present invention relates to implantable medical devices and methods, and more particularly, to a dual-chamber implantable pacemaker or pacemaker system having enhanced upper rate behavior adapted to maintain a more appropriate ventricular frequency and to minimize the risk of a pacemaker-mediated tachycardia (PMT).

The basic function of the heart is to pump (circulate) blood throughout the body. The blood serves as a medium for delivering oxygen and nutrients to the various tissues while removing waste products and carbon dioxide. The heart is divided into four chambers comprised of two atria and two ventricles. The atria are the collecting chambers holding the blood which returns to the heart until the ventricles are ready to receive this blood. The ventricles are the primary pumping chambers. The pumping function of the heart is achieved by a coordinated contraction of the muscular walls of the atria and the ventricles.

The atria are more than simple collecting chambers. The atria contain the heart's own (natural, native or intrinsic) pacemaker that controls the rate at which the heart beats or contracts. In addition, the atrial contraction helps to fill the ventricle, further contributing to optimal filling and thus maximizing the amount of blood which the heart is able to pump with each contraction. Thus, atrial contraction is followed after a short period of time (normally 120 to 200 ms) by ventricular contraction.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This is termed AV synchrony.

A cardiac cycle comprises one sequence of systole and diastole. It can be detected by counting the patient's pulse rate. It is also reflected by the cardiac rhythm as recorded by an electrocardiogram (ECG) or electrogram (EGM). The ECG is a recording of the electrical activity of the heart as seen using surface electrodes placed on the surface of the body. The EGM is a recording of the electrical activity of the heart as seen using electrodes placed within the heart. The electrical activity refers to the cardiac depolarization in either the atrium and/or ventricle. In general, on the ECG or EGM, the atrial depolarization is represented by a P-wave, while the ventricular depolarization is represented by a QRS complex, sometimes abbreviated as an "R-wave." The electrical depolarization triggers or initiates the active muscular contraction. Once the cardiac cells are depolarized, they must repolarize in order for the next depolarization and contraction to occur. Ventricular repolarization is represented by the T-wave. Atrial repolarization is rarely seen on an ECG or EGM as it occurs at virtually the same time as the R-wave, and is thus hidden by this large electrical signal.

A normal heart rate varies between 60 to 100 (bpm) with an average of 72 bpm resulting in approximately 100,000 heart beats per day. The heart beat normally increases during periods of stress (physical or emotional) and slows during periods of rest (sleep).

The amount of blood that the heart pumps in one minute is called the cardiac output. It is calculated by the amount of blood ejected with each heart beat (stroke volume) multiplied by the number of heart beats in a minute. If the heart rate is too slow to meet the physiologic requirements of the body, the cardiac output will not be sufficient to meet the metabolic demands of the body. Too slow of a heart rate, termed a bradycardia, may thus result in one of two major symptoms: (1) if the heart effectively stops with no heart beat, there will be no blood flow and if this is sustained for a critical period of time (10 to 30 seconds), the individual will faint; or (2) if there is a heart beat but it is too slow, the patient will be tired and weak (termed low cardiac output).

A pacemaker is a medical device that is used to selectively stimulate the heart with electrical stimulation pulses aimed at assisting it to perform its function as a pump. Normally, the stimulation pulses are timed to keep the heart rate above a prescribed limit, i.e., to treat a bradycardia. A pacemaker may thus be considered as a pacing system. The pacing system is comprised of two major components. One component is a pulse generator which generates the stimulation pulse and includes the electronic circuitry and the power cell or battery. The other is the lead or leads which electrically couple the pacemaker to the heart.

The pacemaker delivers an electrical stimulus to the heart to cause the heart to contract when the patient's own intrinsic rhythm fails. To this end, pacemakers include sensing circuits that sense the EGM, and in particular that sense the P-waves and/or R-waves in the EGM. By monitoring such P-waves and/or R-waves, the pacemaker circuits are able to determine the intrinsic rhythm of the heart and provide stimulation pulses that force atrial and/or ventricular depolarization at appropriate times in the cardiac cycle so as to help stabilize the electrical rhythm of the heart.

Pacemakers are described as either single-chamber or dual-chamber systems. A single-chamber system stimulates and senses the same chamber of the heart (atria or ventricle). A dual-chamber system stimulates and/or senses in both chambers of the heart (atria and ventricle). Dual-chamber systems may typically be programmed to operate in either a dual-chamber mode or a single-chamber mode.

A three letter code (sometimes expanded to a five letter code) is used to describe the basic mode in which the pacemaker is operating. These three letters refer specifically to electrical stimulation for the treatment of bradycardia. A fourth position (when used) identifies the degree of programmability and rate modulation, and a fifth position (when used) refers to electrical stimulation therapy for the primary treatment of fast heart rhythms or tachyarrhythmias or tachycardias.

The first position of the pacemaker code identifies the chamber to which the electrical stimulus is delivered. If the device is not capable of bradycardia support pacing, a "0" occupies this first position. If the unit paces in the ventricle, this is identified by a "V"; if it paces in the atrium, the first position is identified as an "A." If stimuli can be delivered to either the atrium or ventricle, the letter "D" is used to reflect dual-chamber stimulation.

The second position of the pacemaker code identifies the chamber or chambers in which sensing occurs. Sensing is the ability of the pacemaker to recognize the intrinsic electrical activity of the heart. The letters used in this position are identical to those used in the first position.

The third position of the pacemaker code identifies the way the pacemaker responds to a sensed signal. An "I" means that the pacemaker will be inhibited. When it senses or sees an intrinsic electrical signal, it inhibits its own output pulse and resets one or more internal timers within the pacemaker's circuitry. The other basic response is represented by a "T," which means triggered. The triggered mode of response indicates that when the pacemaker senses an intrinsic electrical signal, it not only resets various internal timers within the pacemaker, it also initiates or releases a stimulus in response to that sensed event. A "D" in the third position refers to both modes of sensing response. Most commonly, a sensed signal arising from the atrium and sensed on the atrial channel of a dual-chamber pacemaker will inhibit the atrial output but trigger a ventricular output after a brief delay (the AV delay). If a native ventricular depolarization does not occur before the AV delay timer completes, a ventricular stimulus will be released at the end of this AV delay. If a native ventricular signal is sensed within the AV delay, the ventricular output will be inhibited and other timers will be reset. If a native ventricular signal is sensed before the atrial stimulus is released, both the atrial and ventricular output pulses will be inhibited and the various timers will be reset.

A popular mode of operation for dual-chamber pacemakers is the DDD mode. DDD systems were developed to overcome the limitations of previous pacing methods. Specifically, DDD systems provide atrial pacing during atrial bradycardia, ventricular pacing during ventricular bradycardia, and atrial and ventricular pacing during combined atrial and ventricular bradycardia. In addition, DDD systems provide an atrial synchronous mode. Such features more closely approximate the normal response to exercise, or other physiological activity demanding a faster heart rate, by permitting a rate increase to occur commensurate with the rate of the sensed P-wave. This advantageously increases cardiac output and facilitates maintenance of AV synchrony.

Unfortunately, a pacemaker operating in the DDD mode may contribute, in combination with other factors, to a pacemaker-mediated tachycardia (PMT). For example, in patients who are prone to atrial arrhythmias, e.g., a fast atrial rate, the DDD pacer tracks the fast atrial rate, causing the ventricles to be paced at a correspondingly fast rate, thereby causing a tachycardia (fast heart rate) to occur. Without the DDD pacemaker, such tachycardia would probably not occur because the ventricles would normally continue at a slower (more normal) rate, despite the fast atrial rate. However, with the DDD pacemaker, the stimulation of the ventricles occurs so as to track the fast atrial rate, and thus the pacemaker effectively intervenes or "mediates" so as to cause the tachycardia, appropriately termed a "pacemaker-mediated tachycardia," or PMT, to occur.

There are also other reasons why a PMT may be triggered by a DDD pacer, other than simply tracking a fast atrial rate. For example, prolonged intervals between atrial and ventricular depolarization can cause or enhance retrograde conduction of P-waves, which retrograde P-waves are sensed by the pacemaker sensing circuits. Unfortunately, the pacemaker sensing circuits cannot differentiate between retrograde P-waves or normal P-waves, so such sensing may result in a PMT wherein each ventricular paced event is followed by a retrograde P-wave which is tracked, resulting in another ventricular paced event, causing the process to repeat.

It is well known that the type of PMT described above (resulting from sensing retrograde P-waves) can be prevented by programming the post ventricular atrial refractory period (PVARP) of the pacemaker to be longer than the retrograde conduction time. Such lengthening of the PVARP, however, disadvantageously prevents the sensing of a P-wave that occurs late in the PVARP. A failure to sense a P-wave, in turn, causes an atrial stimulus to be generated by the pacemaker that is more than likely delivered into the heart's atrial refractory period, at a time when such pulse is ineffective. This results in an effective prolongation of the P-to-V interval, which may either decrease hemodynamic performance and/or induce retrograde conduction. Even worse, the possibility exists that the atrial stimulus (delivered into the heart during the atrial refractory period) may induce atrial flutter or fibrillation. It is thus apparent that what is needed is a dual-chamber pacemaker that enhances its upper rate behavior so as to assure that any atrial stimulus will be effective, thereby minimizing the risk of retrograde conduction and induction of a PMT or atrial arrhythmias. There is also a need, in enhancing the upper rate response, to assure that pathological atrial rhythms are not tracked, thereby providing a more appropriate ventricular rate.

Several approaches are known in the art to minimize the likelihood of a PMT in patients having a dual-chamber pacing system. For example, for patients who are particularly prone to atrial arrhythmias and where tracking of fast atrial rates is not desirable, the pacing system can simply be programmed to operate in a DDI mode. The DDI mode operates the same as the DDD mode except that the atrial signals (P-waves) are not tracked. Hence, detection of P-waves in the DDI mode results in inhibition of atrial output, with normal ventricular timing. Thus, reversion to DDI pacing has proven to be an effective technique for minimizing the likelihood of PMT's for such patients.

Unfortunately, when pacing in the DDI mode, a sensed P-wave may result due to retrograde conduction, and therefore occur at a time in the cardiac cycle that is not hemodynamically efficient, i.e., at a time that is not appropriately synchronized with the next scheduled ventricular stimulation. That is, a hemodynamically efficient P-wave is one that occurs at a time in the cardiac cycle that provides "atrial kick" to fill the ventricles with blood just prior to the delivery of the next ventricular stimulation pulse pursuant to the pacemaker-determined ventricular timing (which is not altered by a sensed retrograde P-wave). It would be desirable, therefore, to provide a modified DDI response that improves the hemodynamic performance of the patient's heart, providing the needed "atrial kick" when appropriate, and not providing it when not appropriate.

SUMMARY OF THE INVENTION

The present invention advantageously addresses the above and other needs by providing a dual-chamber implantable pacemaker operable in the DDD mode that automatically reverts to a modified DDI mode whenever a P-wave is sensed within a prescribed time interval following the pacemaker's post-ventricular atrial refractory period (PVARP). Advantageously, the pacemaker's PVARP may assume short or long values, as might occur, e.g., during rate-responsive pacing, while still preventing tracking of retrograde conduction. When initiated, the modified DDI mode advantageously generates an additional atrial stimulation pulse (thereby providing additional atrial kick) only if there is sufficient time left in the current cardiac cycle for the additional atrial kick thus provided to be of hemodynamic benefit.

In accordance with one aspect of the invention, the timing circuits included within the dual-chamber pacemaker define a time interval or "time window," $T_A$, that follows the post-ventricular atrial refractory period (PVARP) of the pacemaker. If a P-wave is sensed during the time window, $T_A$, the modified DDI mode is automatically initiated. In such modified DDI mode, the time between the last ventricular event and the next scheduled ventricular pulse, absent the detection of an inhibiting R-wave, is not changed. Further, if there is sufficient time to supply an atrial pulse before the next ventricular pulse is scheduled, such atrial pulse is generated to provide additional atrial kick.

In operation, the manner in which the above determination is made (whether there is sufficient time to supply an atrial pulse) is as follows: if there is more than a prescribed time period, $T_P$, remaining before the next atrial pulse is scheduled after having sensed a P-wave, then an A-pulse will be generated. If there is not more than the $T_P$ period remaining before the next atrial pulse is scheduled after having sensed a P-wave, than no A-pulse is generated.

During the modified DDI mode, when a determination is made that an A-pulse is to be generated, it is preferably delivered x msec before the ventricular pulse, where x is a programmed number that is usually equal to, or somewhat less than, the pacemaker's AV Delay (AVD). Advantageously, x and/or the AVD may be either a programmed value, or an adaptive value that varies as a function of a parameter sensed by a rate-responsive sensor (when the pacemaker is operating in a rate-responsive mode).

If no P-wave is sensed during the time window $T_A$, then normal DDD pacing continues. Further, when a P-wave is sensed during $T_A$, causing reversion to the modified DDI mode as described above, such modified DDI mode continues only to the end of the pacing cycle. During the next pacing cycle, the modified DDI mode is initiated again only if a P-wave is sensed during the time window $T_A$, otherwise DDD pacing continues. In other words, the present invention, when invoked, starts each pacing cycle in the DDD mode, and reverts to the modified DDI mode only if a P-wave is sensed during the time window $T_A$.

In accordance with one embodiment, the invention may be characterized as a DDD pacemaker system that stimulates the heart of a patient. Such pacemaker system includes an atrial channel that has means for sensing P-waves and means for generating and delivering atrial stimulation pulses (A-pulses), and a ventricular channel that has means for sensing R-waves and means for generating and delivering ventricular stimulation pulses (V-pulses). The pacemaker system also includes control means for controlling the atrial channel and the ventricular channel to operate in a DDD mode of operation. More particularly, the control means includes: (1) timing means for defining a pacing cycle made up of a plurality of timing periods, each timing period including a post ventricular atrial refractory period (PVARP) that begins with a ventricular event (a sensed R-wave or a generated V-pulse); and (2) means for temporarily reverting from the DDD mode of operation to a modified DDI mode of operation. Such temporary reversion occurs only if a P-wave falls into a predetermined time period following the PVARP. Such modified DDI mode is characterized by generating an A-pulse within the atrial channel if a first time period $T_P$ elapses after the P-wave was sensed and a second time period, AVD, yet remains prior to the next scheduled V-pulse.

The present invention may further be viewed as a DDD pacemaker that stimulates the atrium of a patient's heart with an A-pulse in a way that assures that the A-pulse thus generated is effective at stimulating the atrium, i.e., that assures that any generated A-pulses are not delivered to the atrium at a time when the atrium is refractory following a natural depolarization.

Similarly, the invention may be seen as such a DDD pacemaker that stimulates the heart of a patient in a way that prevents the pacemaker from tracking inappropriate atrial depolarizations associated with retrograde conduction, atrial flutter, or atrial fibrillation.

The invention may also be depicted as a method of operating a dual-chamber implantable pacemaker. Such method comprises sensing when an atrial depolarization (P-wave) and a ventricular depolarization (R-wave) occur within a patient's cardiac cycle, and generating an atrial stimulation pulse (A-pulse) and/or a ventricular stimulation pulse (V-pulse) in accordance with a modified DDD mode of operation. The modified DDD mode of operation comprises a normal DDD operation that reverts to DDI operation upon the occurrence of certain events. A normal DDD operation is characterized by generating an atrial escape interval (AEI) and an A-V delay (AVD), with the AEI and AVD each being of a preset maximum duration, and by defining a pacing period as the AEI followed by the AVD, and generating an A-pulse at the conclusion of the AEI only if a P-wave is not sensed during the AEI, and terminating the AEI immediately upon sensing a P-wave, and generating a V-pulse at the conclusion of the AVD only if an R-wave is not sensed before the timing-out of the AVD, and terminating the AVD immediately upon sensing an R-wave, thus ending the pacing period and beginning the next pacing period. The method of the invention thus includes modifying the above DDD operation by reverting to a modified DDI operation in the event a P-wave is sensed within a predetermined time window within the pacing period. Such modified DDI operation is carried out by: (1) preserving the time between the last ventricular event and the next scheduled V-pulse, absent the sensing of an R-wave, and (2) generating an A-pulse if there remains sufficient time within the pacing period for such A-pulse to be generated at least a prescribed time interval after the sensing of a P-wave and at least one AVD prior to the next scheduled V-pulse.

It is noted that the A-V delay (AVD) described above and utilized by as one of the timing intervals of the pacemaker may be either the delay between an A-pulse and a V-pulse (i.e., an A-pulse-to-V-pulse delay, or "AVD"), or the delay between a sensed P-wave and a V-pulse (sometimes referred to as a "PVD"). For purposes of the invention, the AVD may be the same as the PVD, or the AVD may be slightly different than the PVD. For simplicity, however, such delay is generically referred to hereafter as simply the "AVD" regardless of whether it is the time between a natural atrial event (P-wave) and the subsequent ventricular event (V-pulse), or the time between a paced atrial event (A-pulse) and the subsequent ventricular event.

Thus, it is a feature of the present invention to provide a dual-chamber pacemaker that operates in a DDD mode and that provides an improved response to an atrial tachycardia (fast atrial rhythm).

It is an additional feature of the invention to provide such a pacemaker that minimizes the risk of pacemaker-mediated tachycardia.

It is another feature of the invention to provide a DDD pacing system that assures that an atrial stimulus, when generated, will be effective.

It is a further feature of the invention to provide such a pacemaker that improves its upper rate response, and in particular allows some degree of P-Wave tracking at high physiologic atrial rates.

It is still another feature of the invention to provide such a dual-chamber pacemaker that selectively reverts to a modified DDI mode of operation when a P-wave is detected within a prescribed time window, $T_A$, following the post ventricular atrial refractory period (PVARP).

It is yet another feature of the invention to provide a modified DDI mode of operation for a dual-chamber pacemaker that provides an atrial stimulation pulse (A-pulse), following the sensing of a P-Wave within a prescribed time window $T_A$ after the PVARP, only if there remains at least a prescribed time period $T_P$ after the sensed P-wave before the next scheduled A-pulse.

BRIEF DESCRIPTION OF THE DRAWINGS

The above and other aspects, features and advantages of the present invention will be more apparent from the following more particular description thereof, presented in conjunction with the following drawings wherein:

FIG. 1 is a typical EGM-type waveform illustrating the normal AV synchrony on the heart;

FIG. 2 is a block diagram of an implantable, programmable, dual-chamber pacemaker;

FIG. 4 is a composite timing diagram, including an event waveform with various timing intervals, that illustrates a conventional DDD mode of operation of a dual-chamber pacemaker;

FIG. 5 is a composite timing diagram as in FIG. 4 illustrating a modified DDD operation of a dual-chamber pacemaker in accordance with the present invention; and FIGS. 6-1 and 6-2 show a flowchart that illustrates the sequence of steps carried out by the control logic of the pacemaker of FIG. 2 as the pacemaker is operated in a modified DDD mode of operation in accordance with the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In order to better understand the present invention, reference will first be made to FIG. 1, where there is shown a typical ECG-type waveform illustrating a normal cardiac cycle of a heart. Such waveforms may be obtained using conventional skin-electrode ECG techniques. Alternatively, intracardiac EGM features of modern pacemakers provide similar ECG information through the use of the telemetry features of such pacemakers.

Figures 1, 6:
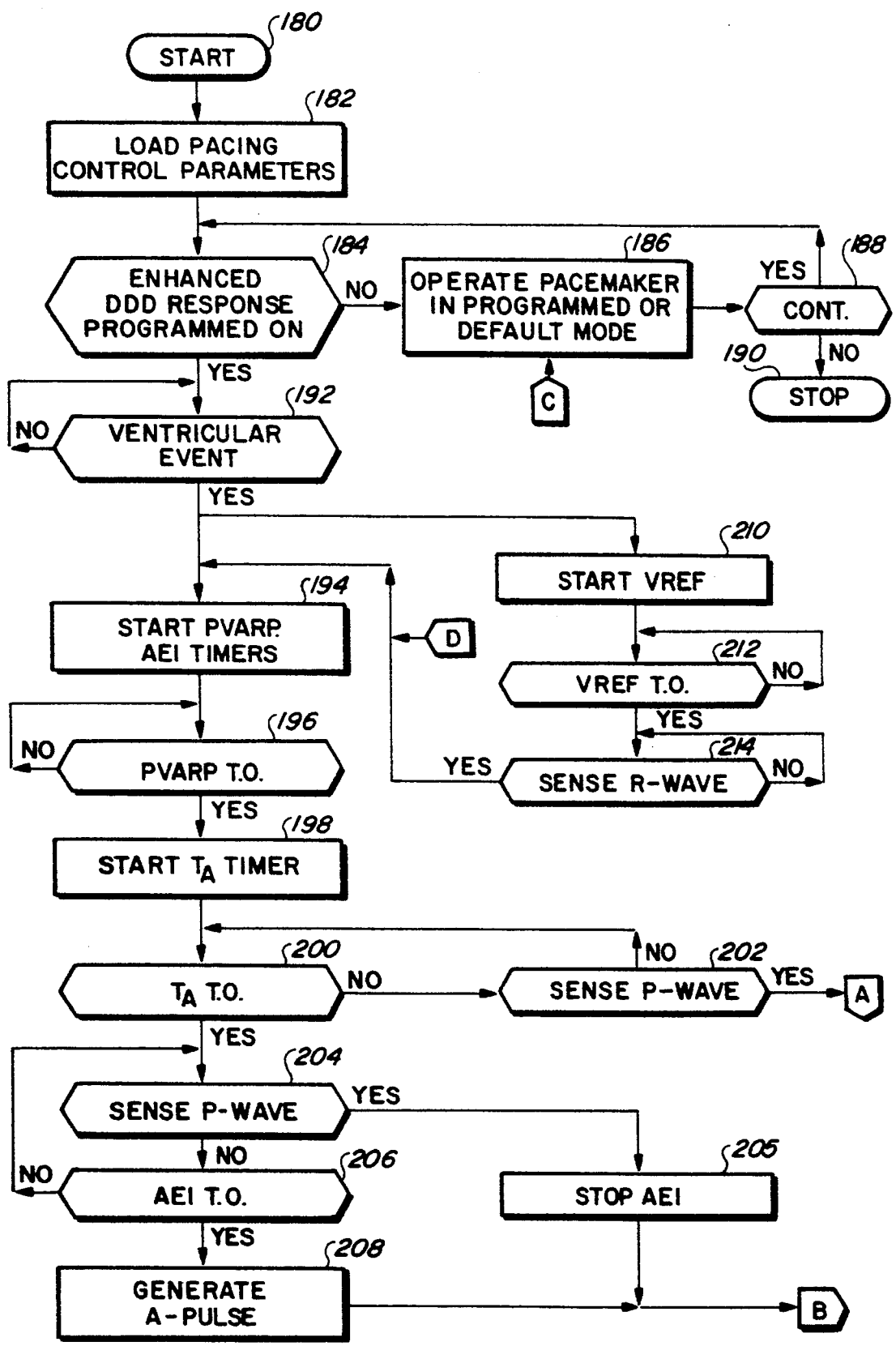

Beginning at the left of the waveform of FIG. 1 there is shown a P-wave. This P-wave represents the electrical activity coincident with the depolarization of the atria of the heart, and the P-Wave may thus be considered as an atrial depolarization signal. Depolarization of the atria is accompanied by the physical contraction of the atria, thereby allowing blood to be pushed from the atria into the ventricles of the heart.

A short time subsequent to the generation of the P-wave, the QRS complex appears, representing the depolarization of the ventricles. The QRS complex is often referred to simply as an R-wave, and such R-Wave may thus be considered as a ventricular depolarization signal. Depolarization of the ventricles is accompanied by the physical contraction of the ventricles, thereby allowing blood to be pushed from the ventricles into the circulatory system of the patient's body. The time period between the P-wave and the R-wave is an important time interval in the operation of the heart because it represents the time needed for proper sequencing of the atria and the ventricles.

The R-wave is followed by a T-wave, which wave represents the electrical activity associated with the repolarization of the ventricles. Both the atrial and ventricular muscle tissue must repolarize before they are capable of depolarizing again. Atrial repolarization occurs a short time after the P-wave, but such repolarization is usually not evident in ECG-type waveforms of the type obtained through skin or intracardiac electrodes because it is masked out by the larger ventricular depolarization signal.

As known to those skilled in the art, the ventricles do most of the work in pumping the blood throughout the body. Typically, one heart beat or heart cycle is measured as the time interval between successive R-waves, simply because the R-wave normally represents the easiest of the waves to identify and measure. A heart beat may, of course, be measured relative to any point within the heart cycle, such as between succeeding T-waves or P-waves.

A certain rhythm or synchrony must occur if the heart is to perform its function of a pump efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricles. If the depolarization of the atria or ventricles do not occur naturally, then a pacemaker may be employed to provide stimulation pulses to these respective heart chambers in order to trigger the required depolarization/contraction at the appropriate time periods of the heart cycle. (Note that the "heart cycle," e.g., the time period between successive ventricular depolarizations, may also be referred to herein as a "pacing cycle," particularly when a pacemaker provides stimulation pulses in order to maintain such cycle.)

When a stimulation pulse is provided to the atrium by a pacemaker, such pulse is referred to herein as an atrial stimulation pulse, or simply an "A-pulse." When a stimulation pulse is provided to the ventricles, such pulse is referred to herein as a ventricular stimulation pulse, or simply a "V-pulse." It is thus the basic function of a pacemaker to monitor the depolarization signals (R-wave and/or P-waves) generated by the heart and provide stimulation pulses when needed within the pacing cycle in order to maintain a desired heart rhythm.

Figures 2, 6:
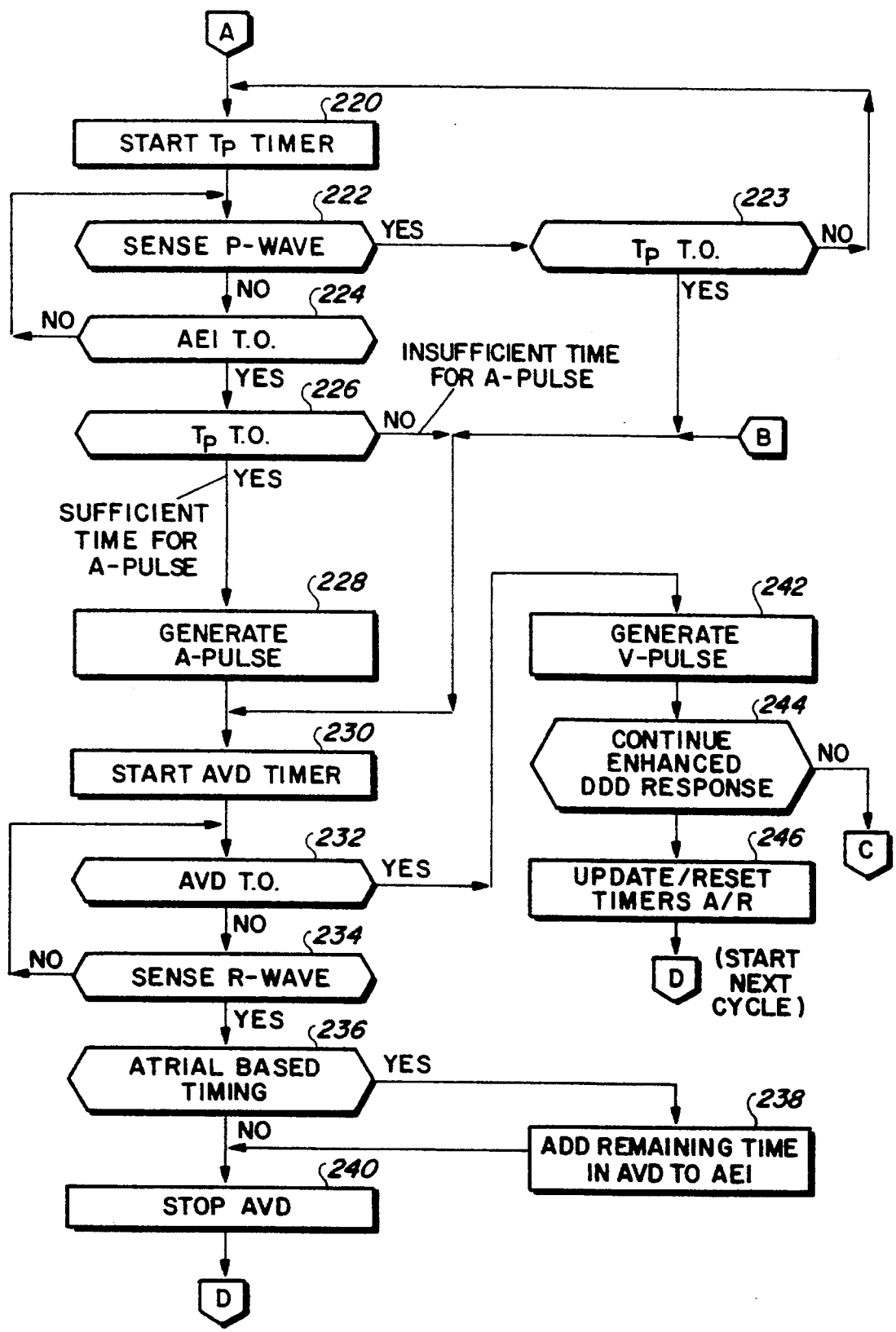

Referring next to FIG. 2, a simplified block diagram of a dual-chamber pacemaker 10 is illustrated. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 are electrically and physically connected to the pacemaker 10 through a connector 13 that forms an integral part of the housing wherein the circuits of the pacemaker are housed. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a control system 26. (Note that throughout this application, the terms "pacemaker" and "pacer" may be used interchangeably.) The control system 26 receives the output signals from the atrial amplifier 22 over signal line 28. Similarly, the control system 26 receives the output signals from the ventricular amplifier 20 over signal line 30. These output signals are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. The atrial trigger signal is referred to simply as the "A-trigger," and the ventricular trigger signal is referred to as the "V-trigger." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, the pacer 10 also includes a memory circuit 40 that is coupled to the control system 26 over a suitable data/address bus 42. This memory circuit allows certain control parameters, used by the control system 26 in controlling the operation of the pacemaker, to be programmably stored and modified, as required, in order to customize the pacer's operation to suit the needs of a particular patient. Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be achieved using any suitable electromagnetic link, such as an RF (radio frequency) channel, a magnetic link, an inductive link, and the like, or any other type of coupling, now known or yet to be developed. Advantageously, through the external programmer 48 and the communication link 50, desired commands may be sent to the control system 26. Similarly, through this communication link 50 and the programmer 48, data (either held within the control system 26, as in a data latch, or stored within the memory 40) may be remotely received from the pacer 10. In this manner, noninvasive communications can be established with the implanted pacer 10 from a remote, non-implanted, location.

The pacer 10 in FIG. 2 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the "atrial channel." Similarly, those portions of the pacer 10 that interface with the ventricles, e.g., the lead 16, the R-wave sense amplifier 24, the V-pulse generator 20, and corresponding portions of the control system 26, are commonly referred to as the "ventricular channel."

A battery 53 is also included within the pacemaker 10 to provide electrical operating power for the pacemaker circuits and for the stimulation pulses (A-pulses and/or V-pulses) that are delivered through the leads 14 and 16 to the heart 12.

In accordance with one embodiment of the present invention, the pacemaker 10 further includes a physiologic sensor 52 that is connected to the control system 26 of the pacer over a suitable connection line 54. While this sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, that is mounted to the case of the pacemaker. Other types of physiologic sensors are also known, such as sensors that sense the oxygen content of blood, respiration rate, pH of blood, body motion, and the like. The type of sensor used is not critical to the present invention. Any sensor that is capable of sensing some physiological parameter that is relatable to the rate at which the heart should be beating can be used. Such sensors are commonly used with "rate-responsive" pacemakers in order to adjust the rate (pacing cycle) of the pacer in a manner that tracks the physiological needs of the patient.

It is noted that the telemetry circuit 44 may be of conventional design, such as is described in U.S. Pat. No. 4,944,299, or as is otherwise known in the art. Similarly, the external programmer 48 may be of any suitable design known in the art, such as is described in U.S. Pat. No. 4,809,697. The '299 and '697 patents are incorporated herein by reference. Likewise, the memory circuit 40, and the circuits utilized in the atrial and ventricular channels may all be of common design as is known in the pacing art. The present invention is not directed to the details of the circuitry utilized for each of these pacing elements. Rather, it is directed to the manner in which all of these pacing elements cooperate with each other in order to provide a particular pacing mode of operation. Such cooperation is provided by the control system 26. Hence, a more detailed description of the control system 26 is presented below.

Figure 3:
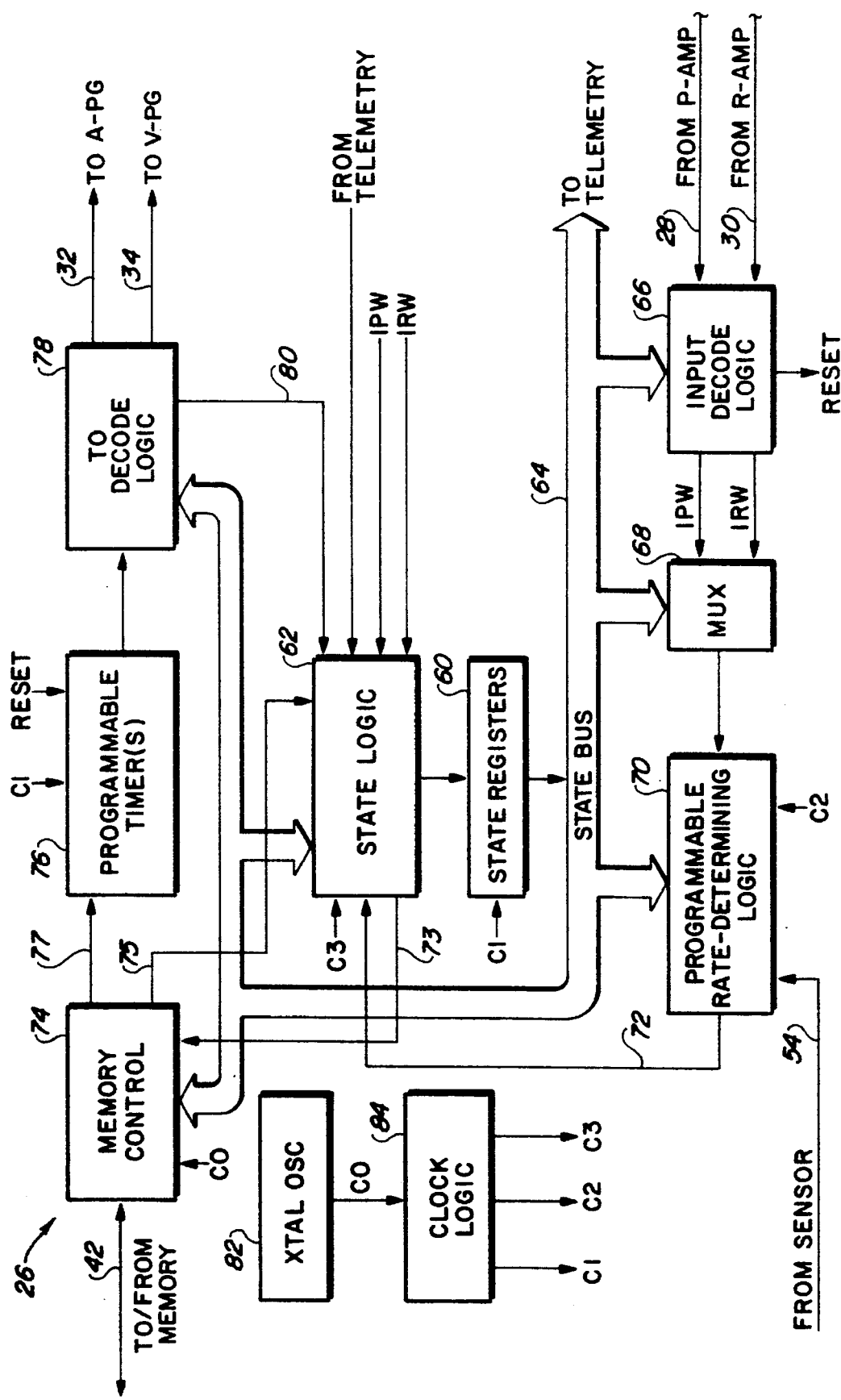
FIG. 3 is a block diagram of one possible embodiment of the control logic of the pacemaker of FIG. 2.

Referring next to FIG. 3, a block diagram of one embodiment of the control system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Rate Response Threshold Adjustment," incorporated herein by reference.

The control system shown in FIG. 3 is based on a state machine wherein a set of state registers 60 define the particular state of the pacer at any instant in time. In general, and as an overview of state machine operation, each state, by design, causes a certain activity or function to be carried out. Several states are executed in a sequence during a given pacing cycle. The sequence of states that is executed in a particular cardiac or pacing cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. When used, such telemetry circuit state machine operates essentially independent of the control system state machine of FIG. 3.

At the heart of the control system 26 is the state logic 62. It is the state logic that controls the "state" of the state registers 60, and hence the function or operation that will next be carried out by the system. The state logic is thus designed to carry out the functions of the invention as described below in connection with FIGS. 4, 5, 6-1 and 6-2. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (Inhibiting P-Wave) and "IRW" (Inhibiting R-Wave) that are selected by a multiplexer 68 and sent to the state logic 62 and to rate-determining logic 70. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1), and (depending upon the particular state of the system, as defined by the state registers 60, and as made available to the rate-determining logic 70 over the state bus 64) sends a sensor signal to the state logic 62 and memory control circuit 74 over signal line 72 indicative of this sensor rate. Such sensor signal may thereafter be used by the state logic 62 for various purposes, including adjustment of the pacing rate.

Still referring to FIG. 3, a memory control circuit 74 provides the needed interface between the circuits of the control system 26 and the memory 40 (FIG. 2). This memory control circuit may be any conventional memory access circuit that sends or receives data to or from memory at a specified address. Data retrieved from memory 40 may be sent to either the state logic 62 (over signal line(s) 75) or to one or more programmable timers 76 (over signal line(s) 77). Data sent to memory 40 may be either the current state of the system (obtained off of the state bus 64), or other selected signals from the state logic (as made available over signal line(s) 73). The function of the programmable timer(s) 76 is to define a prescribed time interval, the length of which is set by the signal(s) received from the memory control 74 and/or from signal line 72 (the sensor signal). Such prescribed time interval is defined by a signal sent over signal line(s) 77, the starting point of which begins coincident with the start of the current state, as obtained from the state bus 64. The timer 76 further generates a time-out (T.O.) signal when this prescribed time interval has elapsed. During this prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-PG 18 or the V-PG 20 (FIG. 2). Further, an appropriate logic signal(s) is sent to the state logic 62 by the time-out decode logic 78 over signal line(s) 80 in order to notify the state logic that the respective trigger signals have been generated.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 Khz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 3 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as an atrial escape interval (AEI) state wherein a prescribed AEI or delay is initiated. As soon as the memory control 74 detects that the AEI state has been initiated, as evidenced by the "1000" appearing on the state bus 64, it retrieves from the memory 40 an appropriate data word, previously programmed into the memory 40 from the external programmer 48, that defines the desired length of the AEI. If rate-responsive pacing is employed, the data word that defines the desired length of the AEI is further modified by the sensor signal. This data word is sent to one of the programmable timers and sets the length of the time period that is to be measured during the AEI state.

The timer(s) 76 is essentially just a counter(s) that counts down (or counts up), using a specified clock signal, to the value specified in the data word. When the counting has been completed, and assuming normal DDD operation, and assuming that the counter has not been reset by the sensing of a P-wave or an R-wave (depending upon the mode of operation of the pacer), the counter or timer 76 is said to have "timed out," and an appropriate time-out signal is generated that is sent to the time-out decode logic 78. (Other types of timers may, of course, also be used, such as are known in the art, including capacitor timing circuits.) The decode logic, in turn, recognizes that the current state of the system is the AEI state (as determined by monitoring the state bus 64), and therefore that the AEI (atrial escape interval) has timed out without any cardiac activity having been sensed. Having made this determination, the decode logic generates an A-pulse trigger signal, sent to the A-PG 18, so that the atrium can be stimulated with an A-pulse. At the same time, an appropriate logic signal(s) is sent to the state logic 62 over the signal line(s) 80 to alert the state logic to the fact that one of the timers 76 has timed out.

The state logic 62, in response to receiving the signal(s) from the time-out decode logic 78, and also in response to the current AEI state, triggers the next state of the prescribed sequence. For most dual-chamber pacing modes, e.g., DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into one of the programmable timer 76. As soon as the timer 76 times-out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an AV Delay (AVD) state.

At the beginning of the AVD state, another value is loaded into one of the programmable timers 76 that defines the length of the AV interval or delay. If the appropriate timer 76 times-out without being reset, indicating that no R-waves have been sensed, the decode logic generates an appropriate trigger signal, e.g., a V-trigger signal, causing a V-pulse to be generated, and notifies the state logic 62 of this event. The state logic, in turn, causes the next appropriate state to be entered, which state may be another blanking state, or BLANK state, similar to the one described above, but having perhaps a different duration. At the conclusion or timing-out of this second BLANK state, the next state in the prescribed sequence is initiated, which state may be a post-ventricular atrial refractory period (PVARP) state.

In the manner described above, the control system 26 assumes one state after another, thereby controlling the operation of the pacemaker. In general, a state is changed when an appropriate one of the timers 76 times-out, or when a prescribed event occurs. For example, if during the AEI state an IPW signal is received (indicating that a P-wave has been sensed), the input decode logic 66 responds appropriately for the given pacing mode. If the pacing mode is a DDD mode, then a reset signal is generated to reset the timer 76, and the state logic 62 responds by immediately (e.g., within the next few clock cycles) changing the state to the next appropriate state, e.g., a PVD state. If the pacing mode is a conventional DDI mode, the timer 76 is not reset. However, the fact that a P-wave occurred is noted so that the generation of an A-pulse at the conclusion of the AEI will be inhibited, as the PVD state begins. Further, if during the PVD state an IRW signal is received (indicating that an R-wave has been sensed), the input decode logic 66 generates another reset signal to reset an appropriate one of the timers 76, and the state logic responds by immediately changing the state to the next appropriate state, e.g., a PVARP state, a VREF state, and/or an AEI state. It is noted that the state of the control system could also be changed by receipt of an appropriate command from the telemetry system.

The control system 26 of FIG. 3 may be realized using dedicated hardware circuits, or by using a combination of hardware and software (or firmware) circuits. The appropriate sequence of states for a given mode of operation, such as DDD or DDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, to U.S. Pat. Nos. 4,712,555 and 4,944,298 wherein a state-machine type of operation for a pacemaker is described; and U.S. Pat. No. 4,788,980, wherein the various timing intervals used within the pacemaker and their interrelationship are more thoroughly described. The '555, '298 and '980 patents are incorporated herein by reference.

It is noted that in the remaining description of the invention that follows, only the main or basic timing intervals that make up the "pacing cycle" will be described. Some common and always-present intervals, such as the blanking intervals that exist after a stimulation pulse is generated, the relative refractory intervals, the maximum tracking interval that defines a maximum tracking rate (MTR), are assumed to be present, but for simplicity are either not shown or not described in detail.

It is also noted that there is a fundamental difference between the "states" described above and the various timing intervals, delays, or periods that make up the pacing cycle. In some instances, a given state will only exist for a given interval, as defined by an appropriate one of the programmable timers. In other instances, however, several time intervals may be timing-out in parallel during a given state, and the duration of the state is determined by events that may or may not happen during such parallel timing. It is convenient, therefore, to describe the present invention in terms of the various "timing intervals" that time-out or are reset during the sequence of events that make up a pacing cycle. Hence, in the description that follows, reference is made to such timing intervals, rather than to "states." Those of skill in the art will be able to design an appropriate pacemaker control system, such as that shown in FIG. 3, that provides pacing cycles made up of the timing intervals described.

Another reason for describing the present invention in terms of "timing intervals" rather than states is that pacing intervals are not dependent upon the type of control system that is used. Thus, the present invention may be practiced regardless of whether the pacemaker is based on a state machine, as shown in FIG. 3, or on a microprocessor-based system, as described in some of the referenced patents, or whether based on other circuit designs that perform the same or similar functions.

Referring then to FIG. 4, there is shown a composite timing waveform diagram that illustrates cardiac depolarization and stimulation signals as a function of selected timing intervals generated within the pacemaker of FIG. 2 when operating in a DDD mode of operation. It is noted that in the composite timing waveform diagram of FIG. 4, as well as the other composite timing waveform diagrams presented herein, time is indicated along the horizontal axis, with an increase or passage of time being represented as movement from left to right in the figure. Several events are shown as separate rows or channels along the vertical axis, including a symbolic representation of certain cardiac events (EVENTS), a post-ventricular atrial refractory period (PVARP), an atrial escape interval (AEI), and an AV delay (AVD). The cardiac events of concern for purposes of the present invention include an R-wave, a P-wave, an A-pulse and a V-pulse. Hence, these are the only events that are shown.

During conventional DDD pacing, as is shown in FIG. 4, a pacing cycle begins with the occurrence of a ventricular event, e.g., an R-wave 102. The pacing cycle includes the AEI followed by the AVD (or PVD). (Note, an AVD follows an A-pulse, whereas a PVD follows a sensed P-wave. In some pacemakers or modes of operation, the AVD may be set to the same value as the PVD; in other pacemakers or modes, there may be a slight difference between the AVD and PVD, e.g, a 25 msec difference. In general, and for simplicity, hereafter the time interval that begins following atrial activity, whether such activity is a P-wave or an A-pulse, will be referred to generically as the "AVD"). As explained below, the AEI and AVD each have an initial programmed value or duration. For rate-responsive pacing, the AEI may be adjusted, e.g., shortened, from this initial or base value as a function of the sensor input. In the absence of natural cardiac depolarization, i.e., in the absence of sensed P-waves or R-waves, the pacing cycle comprises the full programmed (or sensor-shortened) value of the AEI followed by the AVD. The sensing of a P-wave during the timing-out the AEI causes the AEI to be immediately reset, and thus truncated or shortened. Similarly, the sensing of an R-wave during the timing-out of the AVD causes the AVD to be immediately reset, and thus also truncated or shortened.

As shown in FIG. 4, the occurrence of the R-wave 102, or other ventricular event, triggers the start of a PVARP, represented by the horizontal line 104, and the start of an AEI, represented by the horizontal line 106. In the DDD mode, the AEI is allowed to time-out, unless a P-wave or R-wave is sensed before it times-out. If a P-wave is sensed, the AEI is immediately reset, and the AVD begins. The AEI is followed by the AVD, represented in FIG. 4 by the line 108. Typically, the PVARP is of a programmed duration, e.g., 100–300 msec. The AEI in conjunction with the AVD thus define the pacing period or "pacing cycle." Thus, the AEI is computed to be of whatever duration is needed to provide the basic programmed pacing rate of the pacemaker. Alternatively, for rate-responsive pacing, the AEI is computed to be a function of the sensor indicated rate. The AVD is also usually of a fixed (programmed) duration, although as indicated above some pacemaker models allow the AVD to adaptively change depending upon whether a P-wave or A-pulse precedes the AVD, and/or as a function of the sensor indicated rate (if rate-responsive pacing is employed).

It is noted that the timing shown FIG. 4, and in the other timing diagrams presented herein, represents ventricular-based timing, i.e., a timing system that defines the pacing cycle as starting with ventricular activity (an R-wave or a V-pulse). It is to be understood, however, that the present invention is not limited to ventricular-based timing, but also may be used for atrial-based timing modes of operation. In an atrial-based timing system, the basic atrial-event to atrial-event timing is preserved to define the pacing cycle, and many timed events within the pacing cycle begin with a sensed or paced atrial event.

The AEI is usually of much longer duration than the PVARP. Hence, the PVARP will time-out first. In FIG. 4, and the other composite timing waveform diagrams presented herein, when a given time interval times-out, such "timing-out" is indicated by placing an arrow head at the right end of the line that represents the timing interval. Similarly, if some event occurs before the timing-out of the time interval, the occurrence of such event is represented by placing a dot along the line representing the time interval.

The purpose of the PVARP is to prevent sensing of P-waves (or other artifacts or signals in the ECG-type waveform being monitored by the pacemaker, e.g., retrograde conduction, that may be interpreted by the pacemaker as P-waves) during that period after a ventricular event (i.e., "post-ventricular") during which the atrium may still be refractory or repolarizing or other "noise" signals may be present. In conventional DDD pacers, it is known to extend the PVARP to prevent sensing retrograde conduction. Disadvantageously, as described previously, such extension of the PVARP may also prevent sensing of P-waves that should be sensed, thereby causing the pacemaker to respond in an inappropriate manner.

During the first pacing cycle shown in FIG. 4, no cardiac events occur during the timing-out of the AEI 106. Hence, upon the timing-out of the AEI 106, an A-pulse 110 is generated, and the AVD 108 commences. During the timing-out of the AVD 108, no further cardiac events are sensed. Thus, upon the timing-out of the AVD 108, a V-pulse 112 is generated.

The generation of the V-pulse 112 signifies the end of the first pacing cycle and the commencement of the next pacing cycle. Hence, another AEI 116 commences after the V-pulse 112 is generated. During the next pacing cycle, i.e., during the timing-out of the AEI 116, a P-wave 114 occurs. For DDD pacing, such occurrence resets the AEI 116, and inhibits the generation of an A-pulse. The resetting of the AEI 116 triggers the commencement of the next AVD 118. As shown in FIG. 4, no R-wave is sensed during the timing-out of the AVD 118. Hence, upon the timing-out of the AVD 118, a V-pulse 120 is generated. The generation of the V-pulse 120 signifies the ventricular event that ends the current pacing cycle and starts the next pacing cycle.

During the next pacing cycle, another P-wave 122 is sensed. This P-wave 122 resets the AEI, inhibits the generation of an A-pulse, and a new AVD 124 commences. Before the AVD 124 times-out, an R-wave 126 occurs. Such occurrence immediately terminates (resets) the AVD 124 and starts the next cardiac cycle. (In an atrial-based timing system, such R-wave occurrence causes the next AEI to be extended by an amount equal to the time remaining in the AVD at the time the R-wave occurs.) The next cardiac cycle includes an AEI 126, followed by an AVD 128. No P-wave is sensed during the timing-out of the AEI 126, so an A-pulse 130 is generated at the conclusion thereof. However, an R-wave 132 is sensed during the timing-out of the AVD 128, causing the AVD to be reset and immediately terminating the pacing cycle.

Thus, as seen in FIG. 4, four of five possible types of pacing cycles are illustrated for DDD operation. (The fifth type of pacing cycle, not shown, is a premature ventricular contraction, or PVC.) The first pacing cycle type includes the A-pulse 110 and terminates with the V-pulse 112; the second includes the P-wave 114 and terminates with the V-pulse 120; the third includes the P-wave 122 and terminates with the R-wave 126; and the fourth includes the A-pulse 130 and the R-wave 132. As further seen in FIG. 4, each pacing cycle is made up of two main timing components: the AEI and the AVD. If no P-waves or R-waves are sensed, the AEI and the AVD are allowed to time-out, an A-pulse and a V-pulse are generated, and the pacing cycle has a duration of AEI+AVD. If an R-wave is sensed, but no P-wave is sensed, the AVD is truncated or cut short, e.g., to a value $AVD_S$, and the pacing cycle has a duration of $AEI+AVD_S$ and an A-pulse is generated at the conclusion of the AEI. (If atrial-based timing is used, then the existence of a truncated $AVD_S$ causes the next cycle to be compensated by extending the AEI to a value $AEI_L$, with the amount of the AEI extension being equal to the amount by which the AVD is truncated.) If a P-wave is sensed, but no R-wave, the AEI is truncated or cut short, e.g, to a value $AEI_S$, and the pacing cycle has a duration of $AEI_S+AVD$, and a V-pulse is generated at the conclusion of the AVD. If both a P-wave and an R-wave are sensed, both the AEI and AVD are cut short, e.g., to a value $AEI_S$ and $AVD_S$, respectively, and the pacing cycle has a duration of $AEI_S+AVD_S$. The shortened values of the AEI and AVD, $AEI_S$ and $AVD_S$, are not fixed values, but are variables that assume a value as a function of when the P-wave or R-wave is sensed relative to when the AEI or AVD were commenced.

Turning next to FIG. 5, a composite timing waveform diagram is shown as in FIG. 4 that illustrates the improved DDD response of the present invention. Basically, as seen in FIG. 5, a ventricular event 140 (which may be either a V-pulse or an R-wave) starts the pacing cycle, triggering the beginning of a PVARP 144 and an AEI 152, as in conventional DDD pacing. The duration of the PVARP for the present invention will typically be somewhat shorter than the duration of the PVARP used for conventional DDD pacing. Further, unlike conventional DDD pacing, as soon as the PVARP 144 times-out, a time window $T_A$ 146 is generated. Typically, the time window $T_A$ will have a value that ranges from about 50 to 200 msec. The $T_A$ value may be fixed, or it may vary as a function of a sensor indicated rate (in the case of rate-responsive pacing). In general, so as to assure that the rate threshold used by the invention is faster than the pacemaker's maximum tracking rate (MTR), it is preferred that AVD, PVARP and $T_A$ be set such that $$AVD+PVARP+T_A \leq 60000/MTR$$

where MTR is expressed in beats per minute and the AVD, PVARP and $T_A$ are expressed in msec. For example, for an MTR of 120 bpm, the AVD could be set to a value of 150 msec, PVARP to a value of 150 msec, and $T_A$ to a value of 200 msec. The above relationship, however, is not a rigid requirement, and in some situations it may be desirable to have the rate set by the sum of the AVD, PVARP and $T_A$ be a rate faster than the MTR.

When a P-wave 142 occurs during the timing-out of the $T_A$ interval 146, as illustrated in FIG. 5, then the present invention reverts to a modified DDI mode of operation. Such modified DDI mode of operation preserves the basic ventricular-event to ventricular-event timing of the pacemaker, i.e., the AEI is not reset. Further, the modified DDI response also produces an A-pulse (to provide additional atrial kick and decrease the potential for retrograde conduction) if sufficient time remains in the cardiac cycle after the P-wave 142 has been sensed for the atria to repolarize before the delivery of the A-pulse, thereby assuring that such A-pulse will be of hemodynamic and electrophysiologic benefit to the patient.

The modified DDI response is illustrated in FIG. 5. The manner in which a determination is made as to whether there is sufficient time remaining in the cardiac cycle for an A-pulse to be of hemodynamic and electrophysiologic benefit is as follows: as soon as a P-wave in sensed within the time window $T_A$, i.e., as soon as the P-wave 142 is sensed within the $T_A$ interval 146, an interval $T_P$ 148 is started. The $T_P$ interval will typically have a value ranging from about 250 to 400 msec, and is preferably about 300 msec. The value of $T_P$ may be a fixed value, or (for a rate-responsive pacer) it may have a value that varies as a function of the sensor signal.

The duration of the $T_P$ interval is selected to allow sufficient time for the atria to repolarize after the depolarization manifest by the sensed P-wave that triggers it. If another P-wave is sensed during the time window $T_P$ interval, then the $T_P$ interval is reset and starts over. Upon the timing-out of the AEI, a determination is made as to whether the $T_P$ interval of the current pacing cycle has timed out. If the $T_P$ interval has timed out, then sufficient time remains for an A-pulse to be of hemodynamic and electrophysiologic benefit to the patient, and such A-pulse is immediately generated, i.e., the A-pulse is generated at the conclusion or timing-out of the AEI. Such A-pulse thus occurs one AVD prior to the next scheduled ventricular event. If the $T_P$ interval has not timed out upon the timing-out of the AEI, then insufficient time remains for an A-pulse to be effective for the patient, and no A-pulse is generated. Rather, the AVD begins upon the timing-out of the AEI, and a ventricular event, i.e., V-pulse, occurs at the timing-out of the AVD, in the absence of sensing an R-wave.

Thus, as seen in the pacing cycle at the left side of FIG. 5, the P-wave 142 occurs during the $T_A$ time window 146, thereby triggering the modified DDI response of the invention. The $T_P$ interval 148 begins immediately upon the sensing of the P-wave 142. The duration of the $T_P$ interval 148 is known, e.g., at a fixed value of about 300 msec. When the AEI 152 times-out, the $T_P$ interval 148 has not yet timed out. Hence, there remains sufficient time for an A-pulse to be generated, and accordingly an A-pulse 150 is generated an interval X 149 prior to the next V-pulse 154. The interval X 149 has a duration of x msec, and may be a programmable value. Typically, the X interval 149 is set equal to, or slightly less than, the AVD 153. In such instance, where the X interval equals the AVD, the A-pulse 150 is thus generated immediately after the AEI 152 times-out. This leaves the interval X 149 equal to the interval AVD 153 between the A-pulse 150 and the next scheduled ventricular event, the V-pulse 154. The generation of the V-pulse 154 (or the sensing of an R-wave, if one occurred) thus signals the end of the modified DDI cycle and the beginning of the next DDD cycle.

The duration of the AVD is designed for maximum hemodynamic benefit to the patient, as it represents the maximum time that should lapse as the blood moves from the atrium to the ventricle for efficient pumping action. Should an R-wave be sensed during the timing-out of the AVD, then such R-wave signals the end of the pacing cycle, no V-pulse is generated, and the next pacing cycle begins.

As seen in the second pacing cycle at the right side of FIG. 5, beginning with the V-pulse 154 (which triggers the beginning of the PVARP 156 and the AEI 164), another P-wave 160 occurs within the $T_A$ window 158 (which window 158 starts after the timing-out of the PVARP 156). In response, another modified DDI response begins. That is, a $T_P$ interval 162 starts immediately upon sensing the P-wave 160. When the AEI 164 times-out, the $T_P$ interval 162 has not yet timed out. Hence, there remains insufficient time for an A-pulse to be generated within the current pacing cycle, and accordingly, no A-pulse is generated. Rather, at the conclusion of the AEI 164, the AVD 166 begins. For the situation shown in FIG. 5, no R-wave is sensed during the timing-out of the AVD 166, so a V-pulse 168 is generated upon the timing-out of the AVD 166, thereby ending the modified DDI response cycle, and beginning the next DDD cycle.

Alternatively, as a programmable option, for the situation shown in the second pacing cycle at the right side of FIG. 5, the start of the AVD 166 may be delayed until the end of the $T_P$ interval 162, with an A-pulse being generated at the conclusion of the $T_P$ interval 162. This option effectively delays the start of the next DDD cycle by an amount of x msec, where x represents the amount of the $T_P$ interval 162 remaining at the timing-out of the AEI 164. This option offers the advantage of preserving some measure of AV synchrony at the expense of either a slightly lengthened pacing cycle or a reduced AVD.

As also seen in FIG. 5, a maximum tracking rate (MTR) interval 170 or 172 is used by the invention that begins upon the timing-out of the $T_A$ interval 146 or 158, respectively. As mentioned previously, the MTR interval, when used, in combination with the PVARP and $T_A$ interval and AVD, define the maximum pacing rate (shortest pacing cycle) that the pacemaker control circuits permit.

Additionally, FIG. 5 depicts a ventricular refractory (VREF) period 174 or 176 that begins upon the occurrence of a ventricular event. During the VREF period, R-waves may not be sensed. The timer used to define the VREF period is a separate timer from the timers used to define the other timing periods, such as the PVARP and AEI, thereby permitting VREF to time-out in parallel with (independent of) the PVARP and AEI periods. Should an R-wave be sensed after the timing-out of the VREF period, then that represents a ventricular event which resets or restarts the pacing cycle.

Turning next to FIGS. 6-1 and 6-2, a flowchart is shown that illustrates the sequence of steps carried out by the control logic of the pacemaker of FIG. 2, or by an equivalent control circuit or pacemaker (e.g., a microprocessor-controlled pacemaker), as the pacemaker is operated in a modified or enhanced DDD mode of operation in accordance with the present invention. Each main step or event that occurs during such sequence is illustrated as a "box" or "block," and each box or block has a reference numeral assigned thereto to facilitate the description of the sequence below.

After starting the sequence (block 180, FIG. 6-1), a first preliminary step involves loading the pacing control parameters into the pacemaker memory (block 182). Such parameters include appropriate parameters that define the initial duration of the PVARP, AEI, $T_A$ interval, $T_P$ interval, MTR, AVD, VREF, the pacemaker's mode of operation, whether the enhanced DDD mode of the present invention is ON or OFF, and other pacing parameters used by the pacemaker. Such parameters are loaded into the pacemaker's memory 40 (FIG. 2) using the telemetry circuit 44 and an external programmer 48 in conventional manner. The control parameters that define the duration of each of the timing intervals are presumed to be data words that are loaded into appropriate timers, as described above in connection with FIG. 3, with such timers starting at an indicated time and timing-out, or stopping, at the prescribed interval thereafter. It is to be understood, of course, that the data words that define the timing intervals may be adjusted, or modified, by a sensor indicated rate, or by other programmed circuitry, depending upon whether a rate-responsive mode of operation is used. It is also to be understood that the use of timers in this manner is not the only way that timing intervals may be defined; and any suitable technique, circuit, software, firmware, or the like, that defines a timing interval may be used with the invention.

Once the memory is loaded with the appropriate control parameters, a determination is made as to whether the enhanced DDD response mode of the present invention has been programmed ON (block 184). If not, then the pacemaker is operated in whatever other mode of operation has been programmed (block 186), or in a default mode of operation. Periodically, or as interrupted by a direct command from the external programmer, a follow-up check is made to see if such mode of operation should continue (block 188), and if not, the sequence stops (block 190). If the mode is to continue, however, or if another mode is to be programmed ON, then another determination is made as to whether the programmed mode is the enhanced DDD response mode (block 184).

If the enhanced DDD response mode is programmed ON (block 184), then such mode looks for the occurrence of a ventricular event (block 192) to signal the beginning of a pacing cycle. In response to the occurrence of a ventricular event, two parallel timing paths (for purposes of the flow chart) begin. In one timing path, the VREF timer is started (block 210) and allowed to time-out (block 212). No R-waves may be sensed during the timing-out of VREF. If an R-wave is sensed after VREF has timed out (block 214), then such R-wave is a ventricular event and the next pacing cycle begins, meaning that the two parallel timing paths begin again. (It is noted, as explained previously in connection with the timing diagrams, that the flow chart of FIGS. 6-1 and 6-2 is a simplified flow chart wherein some time intervals are not discussed or shown, such as the absolute and relative refractory portions of a refractory interval, blanking intervals, and the like, the use of which is well known in the art.)

In the second timing path, commenced after a ventricular event, the PVARP and AEI timers are started (block 194). The PVARP timer is allowed to time-out (block 196). During the PVARP, no P-waves may be sensed. Upon the timing-out of the PVARP timer, the $T_A$ timer is started (block 198). While the $T_A$ timer is timing-out, the atrial channel is monitored to determine whether a P-wave is sensed (blocks 200, 202). If the $T_A$ timer times-out without having sensed a P-wave (YES branch of block 200), then that means a normal DDD operation will be carried out for the remainder of the pacing cycle.

The normal DDD operation for the remainder of the pacing cycle continues as follows: first, a determination is made as to whether a P-wave is sensed before the timing-out of the AEI (blocks 204, 206). If the AEI times-out without a P-wave having been sensed (YES branch of block 206), then an A-pulse is generated (block 208) and the AVD timer commences (block 230, FIG. 6-2). If a P-wave is sensed (YES branch of block 204, FIG. 6-1), then the AEI is immediately reset or stopped (block 205, FIG. 6-1) and the AVD timer (which functions in this instance as a PVD timer) commences (block 230, FIG. 6-2).

If a P-wave is sensed during the timing-out of the $T_A$ interval (YES branch of block 202, FIG. 6-1), then a modified DDI response is started for the remainder of the pacing cycle. Such modified DDI response commences by starting a $T_P$ timer (block 220, FIG. 6-2). During the timing-out of the $T_P$ timer, a determination is made as to whether a P-wave is sensed (block 222). If a P-wave is sensed (YES branch of block 222), then a determination is made as to whether the $T_P$ timer has timed out (block 223), and if not (NO branch of block 223), the $T_P$ timer begins again (block 220). If the $T_P$ timer has timed out (YES branch of block 223), then the AVD timer begins (block 230). If a P-wave is not sensed while the $T_P$ timer is timing-out (NO branch of block 222), and if the AEI timer has not yet timed out (block 224), then the pacer continues to monitor the atrial channel for the occurrence of a P-wave (block 222). In this manner, then, a determination is made as to whether a P-wave occurs during the $T_A$ window (blocks 200, 202, FIG. 6-1) and before the timing-out of the AEI (blocks 220, 222, 224). Any P-waves that are sensed in the $T_A$ window cause the $T_P$ timer to be restarted, unless the $T_P$ timer (started upon the sensing of a prior P-wave) has already timed out.

Once the AEI timer has timed out (block 224), a determination is made as to whether the $T_P$ interval has timed out (block 226). If so (YES branch of block 226), then that means an A-pulse can be generated without pacing into the refractory period of the atrium, and accordingly an A-pulse is generated (block 228) and the AVD timer commences (block 230). If not (NO branch of block 226), then that means an A-pulse would not be effective because the atrium is likely to still be refractory, and accordingly no A-pulse is generated and the AVD timer begins (block 230).

If an R-wave is sensed during the timing-out of the AVD (blocks 232, 234), and assuming that atrial-based timing is not used (NO branch of block 236), then the sensed R-wave causes the AVD to be terminated (block 240), and the next pacing cycle begins (at connector "D" in FIG. 6-1). If atrial-based timing is used (YES branch of block 236), then the time remaining in the AVD interval at the time the R-wave is sensed is added to the AEI for the next pacing cycle (block 238), the AVD is terminated (block 240), and the next pacing cycle begins (at connector "D" in FIG. 6-1), which pacing cycle thus uses an extended AEI.

If the AVD times-out before an R-wave is sensed (YES branch of block 232), then a V-pulse is generated (block 242). Such V-pulse represents a ventricular event that signifies the beginning of a new pacing cycle. As the new pacing cycle begins, a determination is made as to whether the enhanced DDD response mode should continue (block 244). If not, then the pacer is operated in whatever other pacing mode is programmed, or in a default mode (block 186, FIG. 6-1), as described above. If the enhanced DDD mode is to continue, then the time intervals are reset and/or updated as required (block 220). Updating may be required, for example, in the case of rate-responsive pacing where the AEI, as well as the $T_A$ interval and the AVD, may change a slight amount from cycle to cycle, or after n cycles, as a function of a sensor indicated rate signal derived from the physiological sensor (52, FIG. 2). The next pacing cycle then begins (at connector "D" in FIG. 6-1).

In the manner described above, it is thus seen that the present invention provides a dual-chamber pacemaker that operates in an enhanced DDD mode which has an improved response to an atrial tachycardia, i.e., P-waves that occur early in the pacing cycle. Advantageously, such enhanced DDD mode minimizes the risk of pacemaker-mediated tachycardia because long intervals between atrial and ventricular depolarization are reduced, with an extra A-pulse being provided in the pacing cycle to provide extra atrial kick when sufficient time remains in the pacing cycle for such A-pulse to be of benefit.

As further seen from the above description, a pacemaker that includes the enhanced DDD mode of the present invention significantly improves its upper rate response, providing DDD operation when appropriate, thereby allowing some degree of P-wave tracking at high atrial rates, and not providing DDD operation when not appropriate, thereby avoiding P-wave tracking when such tracking might lead to a pacemaker-mediated tachycardia.

As also seen above, a dual-chamber pacemaker operating in accordance with the present invention automatically reverts to a modified DDI mode when a P-wave is detected within a prescribed time window, $T_A$, following the post ventricular atrial refractory period (PVARP). Further, such modified DDI mode advantageously provides an atrial stimulation pulse (A-pulse), following the sensing of a P-wave, if there is sufficient time remaining in the current cardiac cycle for such A-pulse to be delivered after a prescribed time interval ($T_P$) following the sensed P-wave.

While the invention herein disclosed has been described by means of specific embodiments and applications thereof, numerous modifications and variations could be made thereto by those skilled in the art without departing from the scope of the invention set forth in the claims.

What is claimed is:

1. A dual-chamber DDD pacemaker for stimulating the heart of a patient, said pacemaker comprising:

ventricular pulse generating means for generating and delivering a ventricular stimulation pulse (V-pulse) to a ventricle of the patient's heart in response to a ventricular control signal;

atrial pulse generating means for generating and delivering an atrial stimulation pulse (A-pulse) to an atrium of the patient's heart in response to an atrial control signal;

sensing means for sensing natural depolarizations of the patient's heart and generating a P-wave signal in response to sensing an atrial depolarization and an R-wave signal in response to sensing a ventricular depolarization; and control means responsive to said P-wave signal and R-wave signal for defining a pacing cycle and selectively generating said atrial control signal and said ventricular control signal within said pacing cycle based on the amount of time between said P-wave signal and R-wave signal, said control means including assurance means for assuring that the atrial control signal occurs at a time within the pacing cycle such that the resulting A-pulse is effective at stimulating the atrium of the patient's heart, wherein said assurance means within said control means comprises means for generating an atrial control signal within the pacing cycle, and hence an A-pulse, following a P-wave signal of the pacing cycle only when there is more than a prescribed time period $T_P$ remaining within the pacing cycle after the P-wave signal before the next atrial control signal is scheduled to be generated by said control means.

2. The DDD pacemaker of claim 1, wherein said control means comprises:

means for generating an atrial escape interval (AEI) that commences with a ventricular event, said ventricular event comprising an occurrence of either an R-wave signal or the generation of a V-pulse;

means for generating a post ventricular atrial refractory period (PVARP) that also commences with said ventricular event;

means for generating an atrial alert time period $T_A$ that begins at the end of said PVARP;

means for generating an atrial-to-ventricular delay (AVD) that begins at the end of said AEI;

said pacing cycle comprising the AEI followed by the AVD;

means for generating said $T_P$ interval to begin upon the generation of said P-wave signal only if said P-wave signal occurs during said atrial alert time period $T_A$.

3. The DDD pacemaker of claim 2, further including physiological sensor means for sensing a parameter of said patient indicative of an appropriate heart rate of said patient and generating a sensor signal indicative of such parameter, and wherein said control means includes means for adjusting the value of said AEI at the beginning of every n pacing cycles as a function of said sensor signal, where n is an integer of at least one, whereby the duration of said pacing cycle varies as a function of said sensor signal, and whereby said DDD pacemaker comprises a rate-responsive pacemaker.

4. The DDD pacemaker of claim 2, wherein said control means includes means for stopping the AVD in the event an R-wave signal occurs before the timing-out of the AVD and extending the AEI of a next pacing cycle by an amount equal to the time remaining in the AVD when stopped.

5. A DDD pacemaker for stimulating the heart of a patient, said pacemaker comprising:

stimulation means for generating and delivering a ventricular stimulation pulse (V-pulse) to a ventricle of the patient's heart in response to a V-pulse trigger signal, and means for generating and delivering an atrial stimulation pulse (A-pulse) to an atrium of the patient's heart in response to an A-pulse trigger signal;

sensing means for sensing natural depolarizations of the patient's heart and generating a P-wave signal in response to a sensed atrial depolarization and an R-wave signal in response to a sensed ventricular depolarization; and control means responsive to said P-wave signal and R-wave signal for defining a pacing cycle and generating said atrial trigger signal within said pacing cycle only when said P-wave signal does not occur within a first specified time period within said pacing cycle, and for inhibiting the generation of said atrial trigger signal within said pacing cycle whenever said P-wave signal does occur within the first specified time period of said pacing cycle, whereby said control means defines the pacing cycle to track appropriate atrial depolarizations, said control means further including prevention means for preventing said control means from defining a pacing cycle that tracks inappropriate atrial depolarizations associated with retrograde conduction, atrial flutter, and atrial fibrillation.

6. The DDD pacemaker of claim 5, wherein said prevention means comprises means for generating the atrial trigger signal, and hence an A-pulse, at a time within the pacing cycle that follows a P-wave signal only when there is more than a prescribed time period $T_P$ remaining within the pacing cycle after the P-wave signal before the next atrial trigger signal is scheduled to be generated by said control means.

7. The DDD pacemaker of claim 6, wherein said control means comprises:

means for generating an atrial escape interval (AEI) that commences with a ventricular event, said ventricular event comprising an occurrence of either an R-wave signal or the generation of a V-pulse;

means for generating a post ventricular atrial refractory period (PVARP) that also commences with said ventricular event;

means for generating an atrial alert time period $T_A$ that begins at the end of said PVARP;

means for generating an atrial-to-ventricular delay (AVD) that begins at the end of said AEI;

said pacing cycle comprising the AEI followed by the AVD;

means for generating said $T_P$ interval to begin upon the generation of said P-wave signal only if said P-wave signal occurs during said atrial alert time period $T_A$.

8. The DDD pacemaker of claim 7, wherein said control means includes means for stopping the AVD in the event an R-wave signal occurs before the timing-out of the AVD and extending the AEI of a next pacing cycle by an amount equal to the time remaining in the AVD when stopped.

9. A DDD pacemaker system for stimulating the heart of a patient, said DDD pacemaker system including a DDD pacemaker that comprises:

an atrial channel that includes means for sensing P-waves and means for generating and delivering atrial stimulation pulses (A-pulses);

a ventricular channel that includes means for sensing R-waves and means for generating and delivering ventricular stimulation pulses (V-pulses);

control means for controlling the atrial channel and the ventricular channel to operate in a DDD mode of operation, said control means comprising:

timing means for defining a pacing cycle made up of a plurality of timing periods, said timing periods including a post ventricular atrial refractory period (PVARP) that begins with a ventricular event, said ventricular event comprising either a sensed R-wave or a generated V-pulse, and means for temporarily reverting from the DDD mode of operation to a modified DDI mode of operation if a P-wave falls into a predetermined time period following the PVARP, said modified DDI mode being characterized by an A-pulse being generated within said atrial channel if a first time period $T_P$ has elapsed since the P-wave was sensed and a second time period, X, yet remains prior to the next scheduled V-pulse.

10. The DDD pacemaker system of claim 9, wherein said time period $T_P$ comprises a fixed time period of between 250 to 400 msec.

11. The DDD pacemaker system of claim 10, wherein said time period $T_P$ comprises a fixed time period of about 300 msec.

12. The DDD pacemaker system of claim 9, further including a rate sensor coupled to said control means, said rate sensor providing a sensor signal indicative of an appropriate heart rate for the patient, and wherein said time period $T_P$ comprises a variable time period that varies between 250 to 400 msec as a function of said sensor signal.

13. The DDD pacemaker system of claim 9, wherein said second time period, X, comprises a fixed value.

14. The DDD pacemaker system of claim 9, wherein said second time period, X, is equal to an AV delay (AVD) of said DDD pacemaker.

15. The DDD pacemaker system of claim 9, wherein said second time period, X, is less than an AV delay (AVD) of said DDD pacemaker and greater than zero.

16. The DDD pacemaker system of claim 9, further including a rate sensor coupled to said control means, said rate sensor providing a sensor signal indicative of an appropriate heart rate for the patient, and wherein said second time period, X, comprises a variable time period that varies as a function of said sensor signal.

17. The DDD pacemaker system of claim 9, wherein said second time period, X, is greater than a predetermined reference period.

18. The DDD pacemaker system of claim 9, wherein said second time period, X, comprises an AV delay (AVD) of said DDD pacemaker, and wherein said control means includes means for extending the next scheduled V-pulse, when required, so that the AVD always exists between the A-pulse and the next scheduled V-pulse.

19. A dual-chamber implantable pacemaker adapted to operate in a modified DDD mode, the pacemaker comprising: a battery, electronic pacing circuitry powered by the battery, and an output connector electrically connected to the electronic pacing circuitry, the output connector being adapted to be electrically coupled through an atrial lead and electrode to an atrium of a patient's heart, and through a ventricular lead and electrode to a ventricle of the patient's heart, the electronic pacing circuitry including:

an atrial channel coupled to the output connector, including means for generating an atrial stimulation pulse (A-pulse) that is delivered through the atrial lead and electrode to the atrium of the patient's heart, and means for sensing an atrial depolarization signal (P-wave) through the atrial lead and electrode;

a ventricular channel coupled to the output connector, including means for generating a ventricular stimulation pulse (V-pulse) that is delivered through the ventricular lead and electrode to the ventricle of the patient's heart, and means for sensing a ventricular depolarization signal (R-wave) through the ventricular lead and electrode;

timing means for generating a plurality of timing intervals, including a post-ventricular atrial refractory period (PVARP), an atrial escape interval (AEI), an AV delay (AVD), a $T_A$ interval, and a $T_P$ interval, and where the combined duration of the AEI followed by the AVD comprise the period of a pacing cycle; and control means for controlling the operation of the atrial channel, ventricular channel, and timing means so as to control the pacemaker to operate in the modified DDD mode of operation, the modified DDD mode of operation including:

first means for simultaneously starting the PVARP and the AEI upon the occurrence of a ventricular event, where a ventricular event comprises either the generating of a V-pulse or the sensing of an R-wave within the ventricular channel;

second means for commencing the AVD upon either the timing-out or resetting of the AEI, whichever occurs first;

third means for commencing the $T_A$ interval at the conclusion of the PVARP;

fourth means for commencing the $T_P$ interval whenever a P-wave is sensed during the $T_A$ interval;

fifth means for determining if the $T_P$ interval has timed out when the AEI times-out, and if so generating an A-pulse; and sixth means for generating a V-pulse at the timing-out of the AVD, and for inhibiting such V-pulse in the event an R-wave is sensed before the timing-out of the AVD;

whereby, if a P-wave is sensed to have occurred during the $T_A$ interval, an A-pulse is generated in the atrial channel at the timing-out of the AEI if a time period of at least $T_P$ has elapsed since a most recent P-wave was sensed, said time period $T_P$ having a duration that is at least as long as a natural refractory period of the patient's heart following a P-wave.

20. The modified DDD pacemaker, as set forth in claim 19, wherein the interval $T_P$ comprises an interval ranging from 250 to 400 msec.

21. The modified DDD pacemaker, as set forth in claim 20, wherein the interval $T_P$ comprises an interval of about 300 msec.

22. The modified DDD pacemaker, as set forth in claim 19, wherein the electronic circuitry within the pacemaker further includes telemetry means for receiving programmed control parameters, and wherein the timing means includes means for setting the initial duration of the timing intervals as a function of the control parameters, whereby the PVARP, AEI, AVD, $T_A$ and $T_P$ intervals may be programmably set to an initial value.

23. The modified DDD pacemaker, as set forth in claim 22, further including a physiological sensor coupled to the control means that generates a rate signal as a function of a sensed physiological parameter, and wherein the control means includes means responsive to the rate signal for adjusting the initial programmed values of at least one of the timing intervals defined by the timing means.

24. The modified DDD pacemaker, as set forth in claim 23, wherein said control means further comprises means for selectively increasing the AEI of a pacing cycle immediately following a current pacing cycle by an amount equal to the time remaining in the AVD at the time an R-wave is sensed in the ventricular channel.

25. A dual-chamber implantable pacemaker comprising:

an atrial channel including means for sensing a P-wave and means for generating an A-pulse;

a ventricular channel including means for sensing an R-wave and means for generating a V-pulse;

a control system coupled to the atrial and ventricular channels for controlling the operation of the atrial and ventricular channels in accordance with an improved DDD mode of operation;

a memory coupled to the control system having sufficient memory capacity for storing a set of control parameters that define the improved DDD mode of operation;

said control system including:

programmable timing means for defining a set of time intervals as a function of the set of control parameters, said set of time intervals including a post-ventricular atrial refractory period (PVARP), an atrial escape interval (AEI), an AV delay (AVD), and a $T_A$ interval; and logic circuitry responsive to the state of the programmable timing means and to the sensed occurrence of P-waves and R-waves for generating a set of control signals that control the operation of the pacemaker to conform its operation with the improved DDD mode, said logic circuitry including means for:

defining a pacing cycle that begins upon the occurrence of a ventricular event and terminates upon the occurrence of a successive ventricular event, where a ventricular event comprises either the sensing of an R-wave or the generating of a V-pulse, starting the AEI and the PVARP at the beginning of each pacing cycle, starting the $T_A$ interval at the conclusion of the PVARP, sensing whether a P-wave occurs during the $T_A$ interval, and if so, determining whether sufficient time remains within the pacing cycle for an A-pulse to be generated at a time within the pacing cycle that such A-pulse will be effective, and if so, generating such A-pulse at a specified time within the pacing cycle, if a P-wave does not occur during the $T_A$ interval, sensing whether a P-wave occurs after the $T_A$ interval but before the termination of the AEI, and if so, immediately resetting the AEI, and starting the AVD upon the timing-out of the AEI if a P-wave is sensed during the $T_A$ interval, or upon the resetting of the AEI if a P-wave is sensed after the $T_A$ interval, with the AVD terminating upon the earliest occurrence of either the sensing of an R-wave or the timing-out of the AVD.

26. The dual-chamber pacemaker, as set forth in claim 25, wherein the set of time intervals generated by the programmable timer further includes a $T_P$ interval, and wherein the logic circuitry includes means for starting the $T_P$ interval immediately upon the sensing of a P-wave during the $T_A$ interval and determining whether at the timing-out of the AEI, the $T_P$ interval has timed out, and if so, generating an A-pulse.

27. The dual-chamber pacemaker, as set forth in claim 26, wherein the $T_A$ interval has a value ranging from 250 to 400 msec.

28. The dual-chamber pacemaker, as set forth in claim 27, wherein the $T_A$ interval and the PVARP are selected so that the sum of PVARP+$T_A$ define a time interval of from 200 to 450 msec folling a ventricular event during which retrograde conduction is likely to occur.

29. A dual-chamber implantable pacemaker comprising:

sensing means for sensing an atrial depolarization (P-wave) and a ventricular depolarization (R-wave) within a patient's cardiac cycle;

pulse generating means for generating an atrial stimulation pulse (A-pulse) and a ventricular stimulation pulse (V-pulse);

control means for controlling the sensing means and pulse generating means so as to operate the pacemaker in a modified DDD mode of operation, the modified DDD mode of operation being characterized by a pacing period, defined by a sequence that comprises an atrial escape interval (AEI) followed by an AV delay (AVD), and by a post-ventricular atrial refractory period (PVARP) that commences at the beginning of each pacing period concurrent with the AEI, and by an interval $T_A$ that begins upon the termination of the PVARP;

said control means including means for reverting to a modified DDI mode of operation for the duration of the pacing period in the event a P-wave is sensed by the sensing means during the interval $T_A$.

30. The dual-chamber implantable pacemaker, as set forth in claim 29, wherein said control means, when operated in accordance with said modified DDI mode of operation, includes means for causing an A-pulse to be generated by said pulse generating means at a predetermined time within the pacing period only if sufficient time remains in the current pacing period for a predetermined time interval, $T_P$, to have elapsed between the sensing of the P-wave and the predetermined time at which the A-pulse is generated.

31. The dual-chamber implantable pacemaker, as set forth in claim 30, wherein the control means includes means for defining the time interval $T_P$, means for starting the timing-out of the time interval $T_P$ upon the sensing of a P-wave during the interval $T_A$, and means for restarting the timing-out of the time interval $T_P$ upon the sensing of a P-wave thereafter, and means for determining if the time interval $T_P$ has timed out upon the timing-out of the AEI, and if so, generating said A-pulse.

32. The dual-chamber implantable pacemaker, as set forth in claim 30, wherein the predetermined time interval $T_P$ comprises a fixed interval having a value within the range of 250 to 400 msec.

33. A method of operating a dual-chamber implantable pacemaker comprising:

(a) sensing when an atrial depolarization (P-wave) and a ventricular depolarization (R-wave) occur within a patient's cardiac cycle;

(b) generating an atrial stimulation pulse (A-pulse) and a ventricular stimulation pulse (V-pulse) in accordance with a modified DDD mode of operation, a DDD mode of operation being characterized by generating an atrial escape interval (AEI) and an AV delay (AVD), with the AEI and AVD each being of a preset maximum duration, and by defining a pacing period as the AEI followed by the AVD, and generating an A-pulse at the conclusion of the AEI only if a P-wave is not sensed during the AEI, and terminating the AEI immediately upon sensing a P-wave, and generating a V-pulse at the conclusion of the AVD only if a depolarization is not sensed before the timing-out of the AVD, and terminating the AVD immediately upon sensing an R-wave, thus ending the pacing period and beginning the next pacing period; and (c) modifying the DDD operation of step (b) by reverting to a modified DDI mode of operation in the event a P-wave is sensed within a predetermined time window within the pacing period, said modified DDI mode being effectuated by:

(1) preserving the time between the last ventricular event and the next scheduled V-pulse, absent the sensing of an R-wave, and (2) generating an A-pulse if there remains sufficient time within the pacing period for such A-pulse to be generated at least a prescribed time interval after the sensing of a P-wave and at least a second prescribed time interval, X, prior to the next scheduled V-pulse.

34. The method of claim 33, wherein step (c) includes:

defining a post-ventricular refractory period (PVARP) and a time interval $T_A$;

beginning the timing-out of the PVARP upon the occurrence of a ventricular event, a ventricular event comprising either the sensing of an R-wave or the generating of a V-pulse;

starting the timing-out of the time interval $T_A$ immediately upon the timing-out of the PVARP;

determining if a P-wave is sensed during the time interval $T_A$, and if so, determining if sufficient time remains within the pacing period to supply an additional A-pulse that will be effective in stimulating the patient's heart and that may be delivered to the patient's heart at least the second prescribed time interval, X, prior to the next scheduled V-pulse, and if so, generating such additional A-pulse.

35. The method of claim 34, wherein the step of determining if sufficient time remains within the pacing period to supply the additional A-pulse comprises:

starting to time-out a time interval, $T_P$, equal to the prescribed time interval, immediately upon the sensing of a P-wave during the interval $T_A$; and determining if the time interval, $T_P$, has timed out upon the timing-out of the AEI, and if so, generating the additional A-pulse at the timing-out of the AEI, and if not so, not generating the additional A-pulse.

36. The method of claim 35, further including restarting said time interval $T_P$ for every P-wave sensed thereafter during said pacing period.

37. The method of claim 35, wherein the interval $T_P$ comprises an interval having a value within the range of 250 to 400 msec.

38. The method of claim 35, wherein the interval $T_P$ is about 300 msec.

39. The method of claim 38, wherein the PVARP followed by the interval $T_A$ together comprise a composite interval following a ventricular event having a duration most likely to include retrograde conduction.

40. The method of claim 39, wherein the composite interval defined by the PVARP plus the interval $T_A$ has a duration of from 200 to 450 msec.

41. The method of claim 35, wherein said second prescribed time interval X is equal to the AVD.

42. The method of claim 35, wherein said second prescribed time interval is greater than zero and less than the AVD.

43. A method of operating an implantable dual-chamber pacemaker in a modified DDD mode of operation; the dual-chamber pacemaker including an atrial channel having A-pulse generating means and P-wave sensing means; a ventricular channel having V-pulse generating means and R-wave sensing means; control means for controlling the operation of the atrial and ventricular channel in accordance with a prescribed mode of operation, the control means including a plurality of timers that define a plurality of time intervals; and means for programming the control means to operate in accordance with the prescribed mode of operation; the method comprising the steps of:

(a) monitoring the ventricular channel for the occurrence of a ventricular event, the ventricular event comprising either the sensing of an R-wave or the generating of a V-pulse;

(b) commencing the timing-out of a post-ventricular atrial refractory period (PVARP), and an atrial escape interval (AEI) upon sensing a ventricular event in step (a);

(c) starting the timing-out of a predetermined interval $T_A$ at the conclusion of the PVARP;

(d) monitoring the atrial channel during the timing-out of the interval $T_A$ for the occurrence of a P-wave;

(e) in the event a P-wave is sensed during the monitoring of step (d), starting the timing-out of an interval $T_P$, waiting for the AEI to time-out, and determining if the interval $T_P$ has timed out at the timing-out of the AEI;

(f) in the event the interval $T_P$ has timed out at the timing-out of the AEI, generating an A-pulse, and starting the timing-out of an AV delay (AVD);

(g) in the event the interval $T_P$ has not timed out at the timing-out of the AEI in step (e), inhibiting the generation of an A-pulse, and starting the timing-out of the AVD;

(h) in the event a P-wave is not sensed during the monitoring of step (d), but is sensed after the timing-out of the interval $T_A$ and before the timing-out of the AEI, immediately resetting the AEI, inhibiting the generation of an A-pulse at the conclusion of the reset AEI, and starting the timing-out of the AVD;

(i) monitoring the ventricular channel at least during the timing-out of the AVD, and generating a V-pulse if no R-wave is sensed before the timing-out of the AVD;

(j) commencing the timing-out of the PVARP and the AEI upon the occurrence of a ventricular event in step (i), where a ventricular event comprises either the generating of a V-pulse or the sensing of an R-wave; and (k) repeating steps (c)–(j) for so long as the pacemaker is operated in the modified DDD mode of operation.

44. The method of claim 43, wherein the interval comprises an interval having a duration of from 250 to 400 msec.

45. A dual chamber DDD pacemaker for stimulating the heart of a patient, said pacemaker comprising:

sensing means for sensing natural depolarization of the atrium of the patient's heart (P-wave) and depolarization of the ventricle of the patient's heart (R-wave);

control means responsive to said R-wave for defining a pacing cycle and for selectively delivering an atrial stimulation pulse to the atrium of the patient's heart within said pacing cycle based upon the time between the the R-wave and any sensed P-wave following the R-wave; and means for assuring that the atrial stimulation pulse occurs when the atrium is excitable and provides hemodynamically beneficial atrial kick.

46. A dual chamber DDD pacemaker for stimulating the heart of a patient, said pacemaker comprising:

sensing means for sensing natural depolarization of the atrium of the patient's heart (P-wave) and depolarization of the ventricle of the patient's heart (R-wave);

control means responsive to said R-wave for defining a pacing cycle and for selectively delivering an atrial stimulation pulse to the atrium of the patient's heart within said pacing cycle based upon the time between the R-wave and any sensed P-wave following the R-wave; and means for assuring that the atrial stimulation pulse occurs when the atrium is excitable, wherein the pacing cycle occurs independently of such atrial stimulation pulse.

47. A dual chamber DDD pacemaker for stimulating the heart of a patient, said pacemaker comprising:

sensing means for sensing natural depolarization of the atrium of the patient's heart (P-wave) and depolarization of the ventricle of the patient's heart (R-wave);

means for delivering a ventricular stimulation pulse to the ventricle of the patient's heart (V-pulse);

means for defining a ventricular event in response to a delivered V-pulse or a sensed R-wave;

control means responsive to said ventricular event for defining a pacing cycle and for selectively delivering an atrial stimulation pulse to the atrium of the patient's heart within said pacing cycle based upon the time between the ventricular event and any sensed P-wave following the ventricular event; and means for assuring that the atrial stimulation pulse occurs when the atrium is excitable and provides hemodynamically beneficial atrial kick.

* * * * *